United States Patent [19]

Sela

[11] Patent Number: 5,410,413

[45] Date of Patent: Apr. 25, 1995

[54] OPTICAL HEAD PROBE USING A GRADIENT INDEX LENS AND OPTICAL FIBERS

[75] Inventor: Ilan Sela, Haifa, Israel

[73] Assignee: Petrometrix Ltd., Haemel, Israel

[21] Appl. No.: 126,158

[22] Filed: Sep. 24, 1993

Related U.S. Application Data

[63] Continuation-in-part of Ser. No. 107,871, Aug. 18, 1993.

[51] Int. Cl.[6] .......................................... G01N 21/47
[52] U.S. Cl. .................................... 356/446; 385/12
[58] Field of Search .................. 385/12; 128/634, 665; 250/227.23, 227.24, 227.28; 356/128, 133, 432, 436, 440, 446

[56] References Cited

U.S. PATENT DOCUMENTS 5,298,741  3/1994  Klalt et al. .................. 250/227.23

*Primary Examiner*—F. L. Evans
*Attorney, Agent, or Firm*—Mark M. Friedman

[57] ABSTRACT

An optical probe head for determining properties of the sample as a function of the depth of the sample, which is made up of a gradient index lens, at least one face of which is in contact with the sample, a number of transmitting optical fibers, preferably made up of a number of concentrically located sets, for inputting radiation into the gradient index lens in at least two optical locations, a mechanism for cycling the input radiation among the transmitting optical fibers, a receiving optical fiber, preferably centrally located, for receiving reflected radiation and a mechanism for processing the reflected radiation to obtain depth-related reflection information.

7 Claims, 6 Drawing Sheets

OPTICAL HEAD PROBE USING A GRADIENT INDEX LENS AND OPTICAL FIBERS

This is a continuation-in-part of U.S. patent application Ser. No. 08/107,871, filed Aug. 18, 1993.

FIELD AND BACKGROUND OF THE INVENTION

The present invention relates to devices for transmitting light to, and receiving light from, a remote sample to be analyzed, and, more particularly, to optical fiber head probes suitable for multi-purpose applications, such as those involving transmission spectroscopy, light scattering spectroscopy, fluorescence, and index of refraction measurements.

A number of devices which are available for use in the spectral analysis of remote scattering. Various of these devices may be used to measure the reflection, the transmission, the fluorescence or the light scattering from the remote samples.

Such devices are typically made up of three pans. Such systems feature an analyzer, which include a light, or other radiation, source and a detection system. A second component is an optical probe head of an appropriate type, for transmitting the light, or other radiation, to, and receiving it from, a sample. Finally, the systems feature suitable fiber optics, for guiding the light, or other radiation, between the analyzer and the probe head.

The present invention relates to the probe head and specifically to probe head which can be used in conjunction with any of a wide variety of analyzers and fiber optics systems in transmission spectroscopy, Raman spectroscopy, and in index of refraction measurements.

A number of different devices are used for remote sensing. At least one device, described in T. Davidson, D. Tracy, A. Lokshin, K. DeCondre, L. McDermott, The Perkin Elmer Corp. in the Pittsburgh Conference, Atlanta (1993), describes the design of a probe head capable of measuring the absolute transmission signal of the sample. The probe described therein includes dual cells, one of which is for sample while the other is a dummy reference cell. A mechanical shutter is used to alternately block and unblock the sample and reference optical path. Such a probe suffers from a number of disadvantages. First, such a probe is made up of many optical components, such as lenses, a beam splitter, prisms, optical windows, and the like, which make it awkward, expensive and difficult to properly align. Second, the probe is inefficient in that at least ¾ of the signal is lost in the course of double pass through the beam splitter, used to split the beam to the self-reference and sample optical paths.

A typical optical probe head available on the market is disclosed in U.S. Pat. No. 5,044,755 by I. Landa et al. The probe disclosed therein is designed to measure transmission. In this particular design, the light emerging from a fiber bundle is collimated by a lens. The optical ray is then guided through a sample compartment and is reflected back to the same lens which focuses the light into the same fiber bundle. Some of the fibers are used to guide the light into the probe while some of the fibers are used to guide the light out to the detection system.

Another type of probe, used by UOP Guided Wave Inc. and by Galileo Electro-optics Corp., is a transmission probe in which the light emerging/Yom the fiber, whether a single fiber or a fiber bundle, is collimated by a lens which guides the light through the sample compartment. On emerging from the sample compartment, the ray is collected by another lens which focuses the optical ray onto a second output fiber.

Neither of the two probe types described above carries a self-reference channel for use in correcting the fiber optical response.

U.S. Pat. No. 5,112,127 by M. M. Carrabba, disclosed the design of an optical probe head for measuring Raman scattering. The device described therein is made up of many optical elements, including three lenses, a beam splinter, a filter and a prism. The device is difficult to align and is capable of probing only very small sample volumes, which may be adequate for sampling opaque materials but is undesirable for applications involving transparent liquids.

S. D. Schwab and R. L. McCreery, in Anal. Chem. 56, 2199 (1984), disclose a simple design for a Raman probe having no optical elements. A fiber bundle is used, with the inner fiber serving in the excitation while the outer fibers are used to collect the scattered light. To use the device, the bundle tip is simply immersed into the specimen to be sampled. One disadvantage of this probe is that, because of the large acceptance angle of the fibers, the device picks up room light, which, even at very low light levels, can be much stronger than the Raman signal.

There is thus a widely recognized need for, and it would be highly advantageous to have, a multi-purpose probe for use in remote sampling which will be simple and reliable and which will be easy to align and operate.

SUMMARY OF THE INVENTION

According to the present invention, there is provided an optical probe head for determining the index of refraction of a sample, comprising: (a) a gradient index lens, at least one face of which is in contact with the sample; (b) at least one transmitting optical fiber for inputting radiation into the gradient index lens; (c) at least one receiving optical fiber, the at least one transmitting optical fiber and the at least one receiving optical fiber being fixedly held relative to the gradient index lens so that the gradient index lens and the optical fibers are aligned such that radiation input into the gradient index lens by the transmitting optical fiber which is reflected from the interface of the gradient index lens and the sample is received by the at least one receiving optical fiber.

According to another embodiment according to the present invention, there is provided an optical probe head for determining the Raman or fluorescent spectra of a sample, comprising: (a) a gradient index lens, at least one face of which is in contact with the sample; (b) at least one transmitting optical fiber for inputting radiation into the gradient index lens; (c) at least one receiving optical fiber, the at least one transmitting optical fiber and the at least one receiving optical fiber being fixedly held relative to the gradient index lens so that the gradient index lens and the optical fibers are aligned such that radiation input into the gradient index lens by the transmitting optical fiber which is scattered from the sample is received by the at least one receiving optical fiber.

According to yet another embodiment according to the present invention, there is provided an optical probe head for determining the absorption spectrum of a sample, comprising: (a) a gradient index lens at least one face of which is in contact with the sample; (b) a mirror placed so as to reflect radiation coming through the gradient index lens back to the gradient index lens through the sample; (c) at least one transmitting optical fiber for inputting radiation into the gradient index lens; (d) at least one receiving optical fiber, the at least one transmitting optical fiber and the at least one receiving optical fiber being fixedly held relative to the gradient index lens so that the gradient index lens and the optical fibers are aligned such that radiation input into the gradient index lens by the transmitting optical fiber which passes through the gradient index lens and the sample to the mirror is reflected by the mirror through the sample and through the gradient index lens and is received by the at least one receiving optical fiber.

According to still another embodiment according to the present invention, there is provided an optical probe head for determining the absolute transmission or absorption of a sample, comprising: (a) a gradient index lens; (b) a mirror placed so as to reflect radiation coming through the gradient index lens back to the gradient index lens through the sample; (c) a moveable partition located between the gradient index lens and the mirror, the partition serving to alternately block and unblock radiation between the mirror and the gradient index lens; (d) at least one transmitting optical fiber for inputting radiation into the gradient index lens; and (e) at least one receiving optical fiber, the at least one transmitting optical fiber and the at least one receiving optical fiber being fixedly held relative to the gradient index lens so that the gradient index lens and the optical fibers are aligned such that radiation input into the gradient index lens by the transmitting optical fiber which passes through the gradient index lens and the sample to the mirror is reflected by the mirror through the sample and through the gradient index lens and is received by the at least one receiving optical fiber when the moveable partition is not blocking radiation between the mirror and the gradient index lens and such that radiation input into the gradient index lens by the transmitting optical fiber which is reflected from the interface of the gradient index lens and the sample is received by the at least one receiving optical fiber.

According to a further embodiment of the present invention, there is provided an optical probe head, comprising: (a) a gradient index lens, at least one face of which is in contact with the sample; (b) a plurality of transmitting optical fibers for inputting radiation into said gradient index lens in at least two optical locations of said gradient index lens; (c) at least one receiving optical fiber for receiving reflected radiation, said transmitting optical fibers and said at least one receiving optical fiber being fixedly held relative to said gradient index lens; and (d) means for processing said reflected radiation so as to obtain depth-related reflection information.

According to further features in preferred embodiments of the invention described below, the optical fibers are held in a ferule which is connected to the gradient index lens.

According to still further features in the described preferred embodiments the aligning of the optical fibers and the gradient index lens is effected by introducing radiation through one of the optical fibers, moving the optical fibers and the gradient index lens relative to each other until maximum radiation intensity is detected in the other of the optical fibers and fixing the position of the optical fibers and the gradient index.

The present invention discloses devices and methods for determining optical properties related to a remote specimen.

A general object of the invention is to provide an optical probe head suitable for measuring transmission spectra, index of refraction, Raman and Rayleigh scattering, and fluorescence spectra.

A further object of the invention is to provide a simple, inexpensive, rugged and efficient optical probe head suitable for applications in harsh environments.

A further object of the invention is to provide an optical probe head which does not require sample preparation.

A further object of the invention is to provide a probe head with strong stray light rejection.

Another object of the invention is to provide a probe head which can be operated in self-referencing configurations and which can provide absolute signals.

Another object of the invention is to provide a probe utilizing fiber optics for remote in-line measurements, or measurements in hazardous environments.

Another object of the invention is to provide a probe which can be readily miniaturized.

Some or all of these and other objects of the invention are achieved in various embodiments thereof through the utilization of a single gradient index (GRIN) lens which is rigidly connected to the polished side of a fiber optics bundle, and, depending on the exact application in question, through the addition of certain accessories.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a multi-purpose optical head probe which can be used in the remote analysis of various properties.

The principles and operation of a probe head according to the present invention may be better understood with reference to the drawings and the accompanying description which relate to three specific applications of a multi-purpose probe head according to the present invention.

Figure 1:
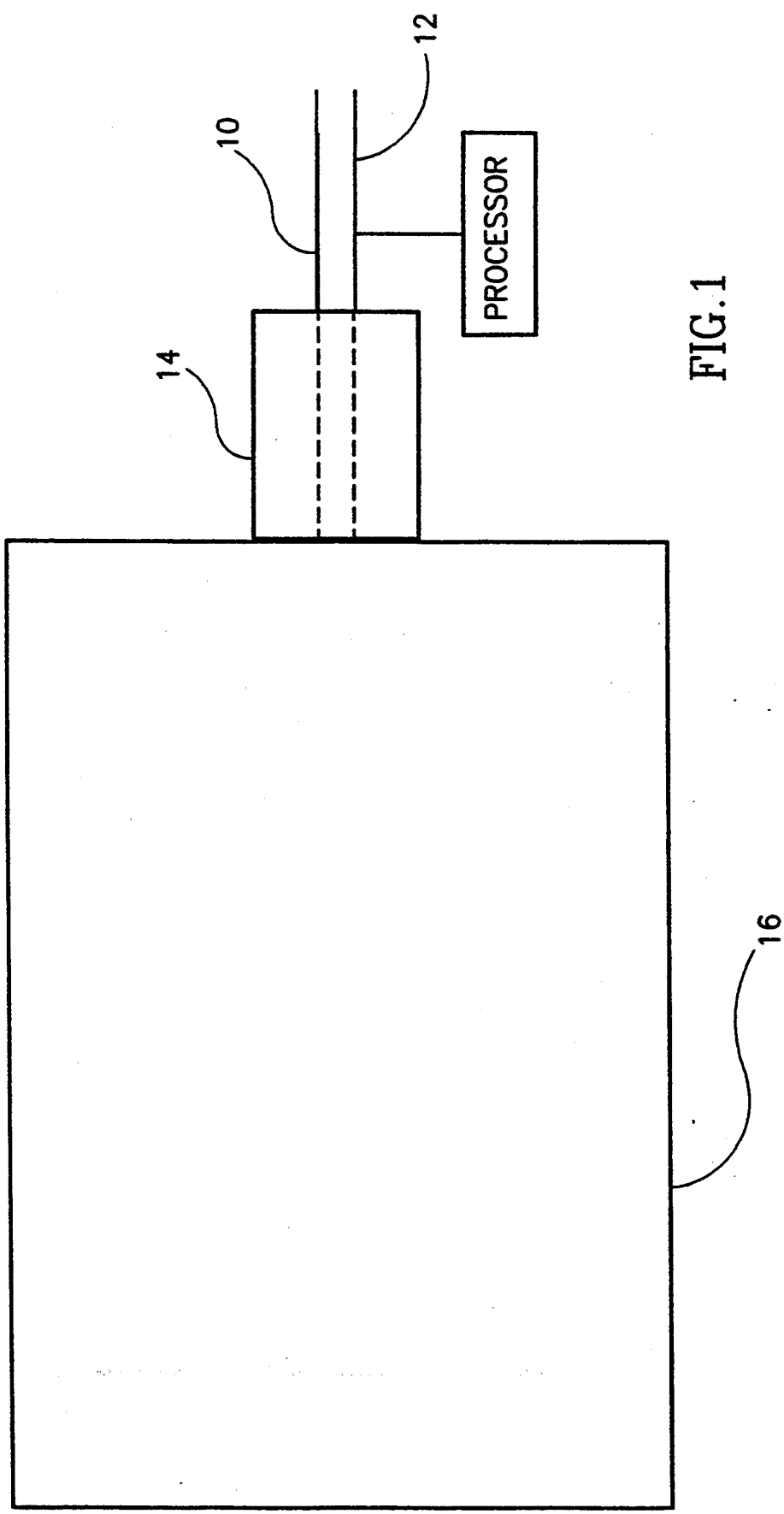
FIG. 1 is a schematic depiction showing the main components of a device according to the present invention.

Referring now to the drawing, FIG. 1 illustrates the basic components of a device according to the present invention. A pair of optical fibers 10 and 12 are inserted in a ferule 14 which is rigidly connected, as by gluing, following alignment as described below, with a gradient index (GRIN) lens 16. The pitch of GRIN lens 16 is chosen so that the light emerging from optical fiber 10 is collimated.

A multi-purpose probe head according to the present invention can be used to determine the index of refraction of a sample. Many instruments are available on the market which are capable of measuring the index of refraction of liquids. Most of them are refractometers which are based on the Abbe, or critical angle refractometer, which has its advantages and disadvantages.

The Abbe, or critical angle, refractometer is a very good hand-operated refractometer and is very accurate and reliable. However, Abbe, or critical angle refractometers, suffer from the limitation that improving their accuracy can be achieved only at the expense of their ability to reject stray light or back scattered light from opaque samples.

At least one refractometer utilizing fiber optics is currently on the market—Model 1430 by Metricor. In this refractometer, carefully characterized light from a light emitting diode (LED) is transmitted to the probe head by a fiber optic cable. Liquid is allowed to flow into the miniature sampling cavity of the probe which acts as a dual refractive surface or tinted mirror. This mirror changes the spectral reflective characteristics of the light source in proportion to the refractive index of the process fluid. The big disadvantage of this technique is that it require considerable handling of the sample before the sample is introduced into the sampling cavity.

A multi-purpose probe head according to the present invention may be used for the remote measurement of the refraction index of fluids. The probe is very accurate, is insensitive to back scattering, is suitable over wide range of refractive indexes, and requires minimal sample preparation. In addition, the probe is very easy to align, can easily be miniaturized and it is optimized for use with fiber optics.

Figure 2:
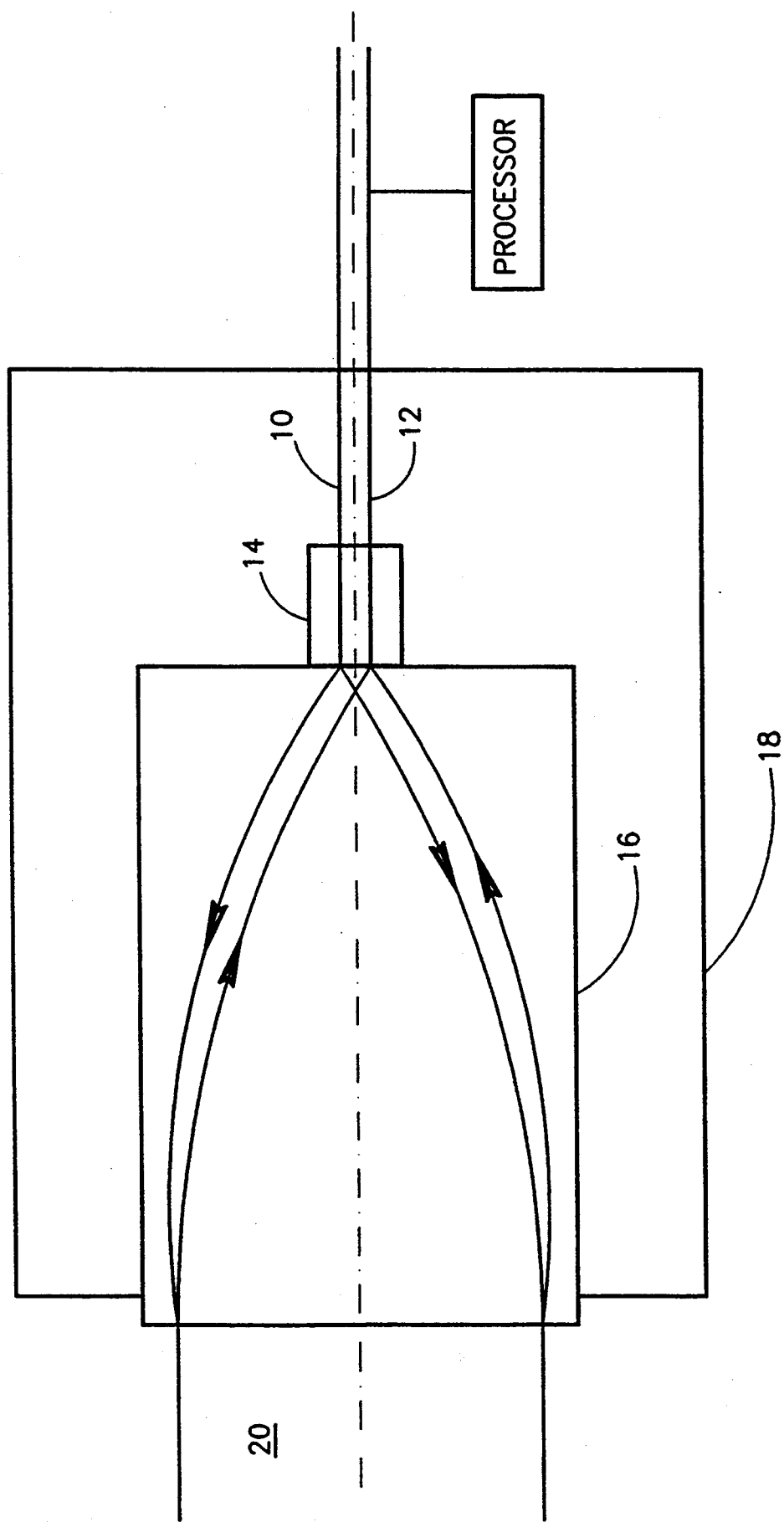
FIG. 2 is a schematic depiction of a device according to the present invention used as an index of refraction optical probe head.

Shown in FIG. 2 is one illustration of a probe as it might appear when serving as a single beam index of refraction optical probe head. As can be seen, the device of FIG. 2 includes the device depicted in FIG. 1 which is partly enclosed in a housing 18. Light from a light source, such as, for example, a light emitting diode, a laser or a lamp, is guided through fiber 10 and emerges from fiber 10 into GRIN lens 16. GRIN lens 16 collimates the light emerging from fiber 10. A portion of the light is reflected back from the interface between the sample 20 and GRIN lens 16. The specular reflected signal is focused back into optical fiber 12 which guides the optical signal to a light sensor (not shown).

As is readily apparent from the description above, it is crucial to properly align the device to ensure that reflected signal is properly focused into optical fiber 12.

The alignment can be effected in a number of ways. Preferably, the alignment is performed as follows. Ferule 14 is temporarily placed up against the surface of GRIN lens 16. A light source (not shown) is used to transmit light through one of the optical fibers, say 10. A detector (not shown) is connected to the end of the other optical fiber, say 12. Ferule 14 is then moved about relative to the surface of GRIN lens 16 until a maximum reading is detected by the light detector, indicting that fibers 10 and 12 and GRIN lens 16 are optimally aligned. At this point, ferule 14 is rigidly connected, preferably by gluing with a suitable adhesive, to the surface of GRIN lens 16, thereby permanently fixing the relative orientation of the components of the device. The proper alignment of the various components ensures that signals emerging from optical fiber 10 and which are reflected from the far surface of GRIN lens 16 are accurately focused into fiber 12.

To calculate the index of refraction of a fluid using a probe as illustrated in FIG. 2, one could proceed as follows. The reflectivity, R, can be derived form the measured reflection signal, $I_r$, and with the appropriate calibration:

$$I_r = I_1 \times F_s \times R$$

where,
$I_1$ is the detector response to the light source signal, and
$F_s$ is the optical attenuation by the system.

Elimination of $I_1 \times F$ can be effected through the prior calibration with known solution, such as pure water.

The reflectivity, R, is, in turn, proportional to:

$$((N_{sample} - N_{GRIN})/(N_{sample} + N_{GRIN}))^2.$$

where,
$N_{sample}$ is the refractive index of the sample, and
$N_{grin}$ is the effective refractive index of the GRIN lens.

Since $N_{GRIN}$ is known, $N_{sample}$ can be deduced from the reflected signal. One advantage of the device is that it is insensitive to the diffuse reflection, or back-scattering from any particulates which might be present in the solution. The reason for this insensitivity is related to the narrow acceptance angle of the fiber optic GRIN lens device.

The acceptance angle of the device depends on the specifications of the GRIN lens as well as on the optical fiber diameter. Assuming that the tested liquid is opaque, or contains metal particulates, and further assuming that the total incident ray is isotopically scattered in all directions, the maximum cone angle of the scattered light accepted by the output fiber can be as low as 4 mrad. The percentage of the incident beam which will be scattered back into the fiber is 0.00004%, which is equivalent to measuring the index of refraction with an accuracy of 4 digits after the decimal point. With a 16 bit A/D stabilized monochromatic light source, such as LED, the index of refraction can be measured over a wide range of refraction indices with an accuracy of better than four digits after the decimal point.

A probe head according to the present invention can be used to measure the transmission spectrum of a sample. For most applications involving quantitative analysis, it is necessary to decouple the net sample absorption from the fiber-analyzer optical response. The optical signal to the analyzer is highly sensitive to various conditions, including light source fluctuations, detector temperature dependence, humidity, fiber condition, and the like. Most systems available today, such as those of UOP Guided Wave Cop. or LT Industries, are self-referencing, incorporating a dual-beam technology, which makes it possible to separate the net sample absorption from the total optical signal. However, in virtually all such systems the reference beam is included in the analyzer enclosure rather than in the optical fiber which guides light to and from the sample probe head. Although this method eliminates the signal dependence on the analyzers optical response it does not eliminate the dependence on optical artifacts originating in the optical fiber.

To further elucidate this point one can distinguish between two cases. Where there is a cable containing a bundle of optical fibers the light signal is uniformly distributed among all the optical fibers. As a result, the influence of each fiber on the signal is reduced by a factor proportional to the number of fibers present in the bundle, which is significant reduction. The disadvantage of such a cable is that it is expansive and economically impractical where the signal must be transported over large distances.

Where a single fiber cable is used the full signal is transmitted through the single fiber. This configuration is most practical for large transmission distances. However, in this case the signal is greatly influenced by fiber conditions, such as bending, temperature and pressure fluctuations, micro cracking, and modes propagation. It is also important to note that for large distances the long optical fiber can absorb as much as 90% of the incoming signal. Therefore, correction for those fiber artifacts are essential to achieve long-term stability and repeatability of the analysis, which can be automatically effected using a probe head according to the present invention.

Figure 3:
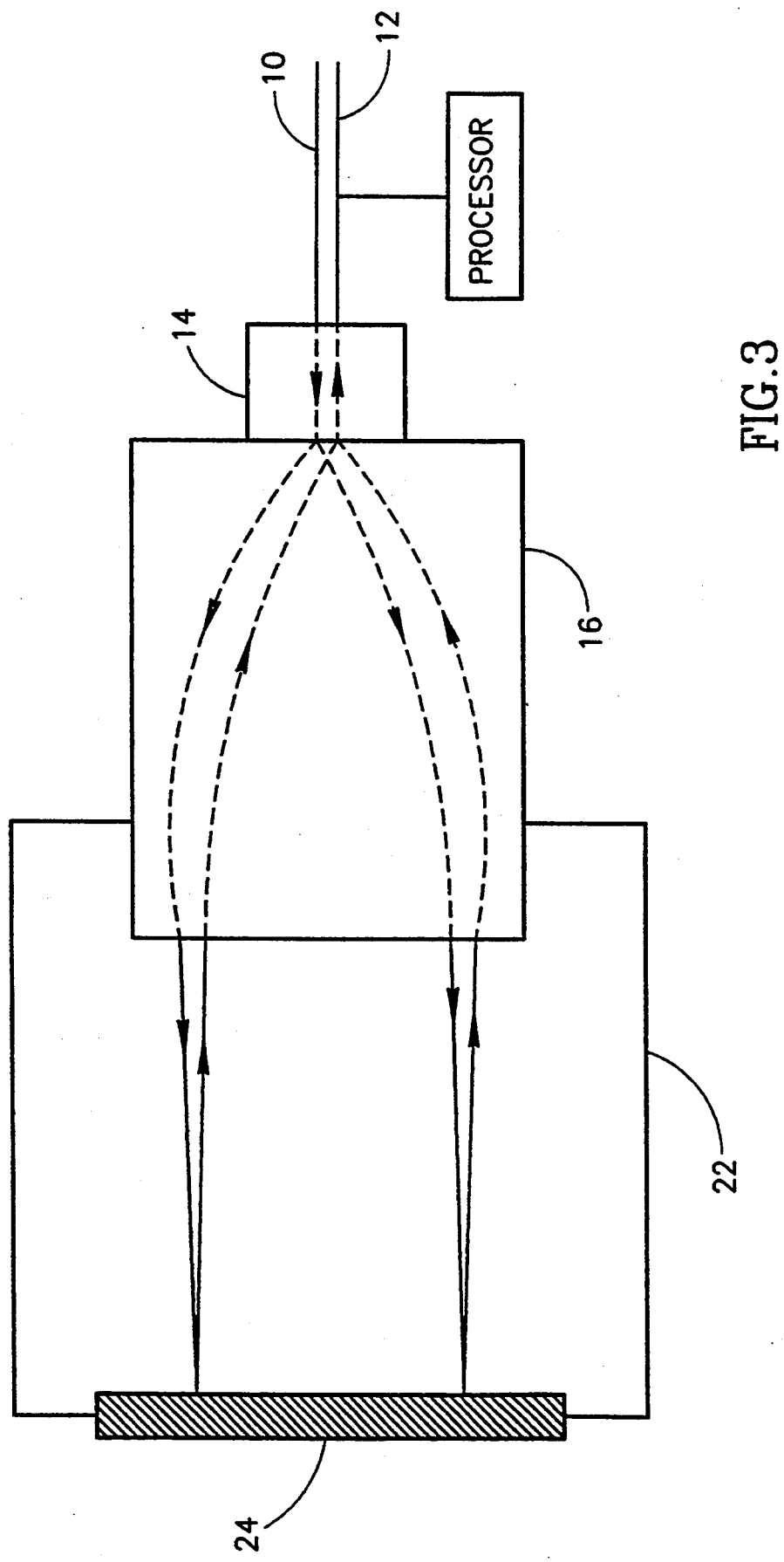
FIG. 3 is a schematic depiction of a device according to the present invention used as a single beam transmission optical probe head.

Shown in FIG. 3 is a probe head according to the present invention for measuring the absorption spectrum of samples. Light from a broad band light source is guided through optical fiber 10. The light is collimated by GRIN lens 16 and passes through a sample compartment 22. At the far end, the light is reflected by a mirror 24 and proceeds to pass through sample compartment 22 and GRIN lens 16 in the reverse sense. GRIN lens 16 focuses the reflected light into optical fiber 12 which guides the light to the signal analyzer system (not shown).

Figure 4:
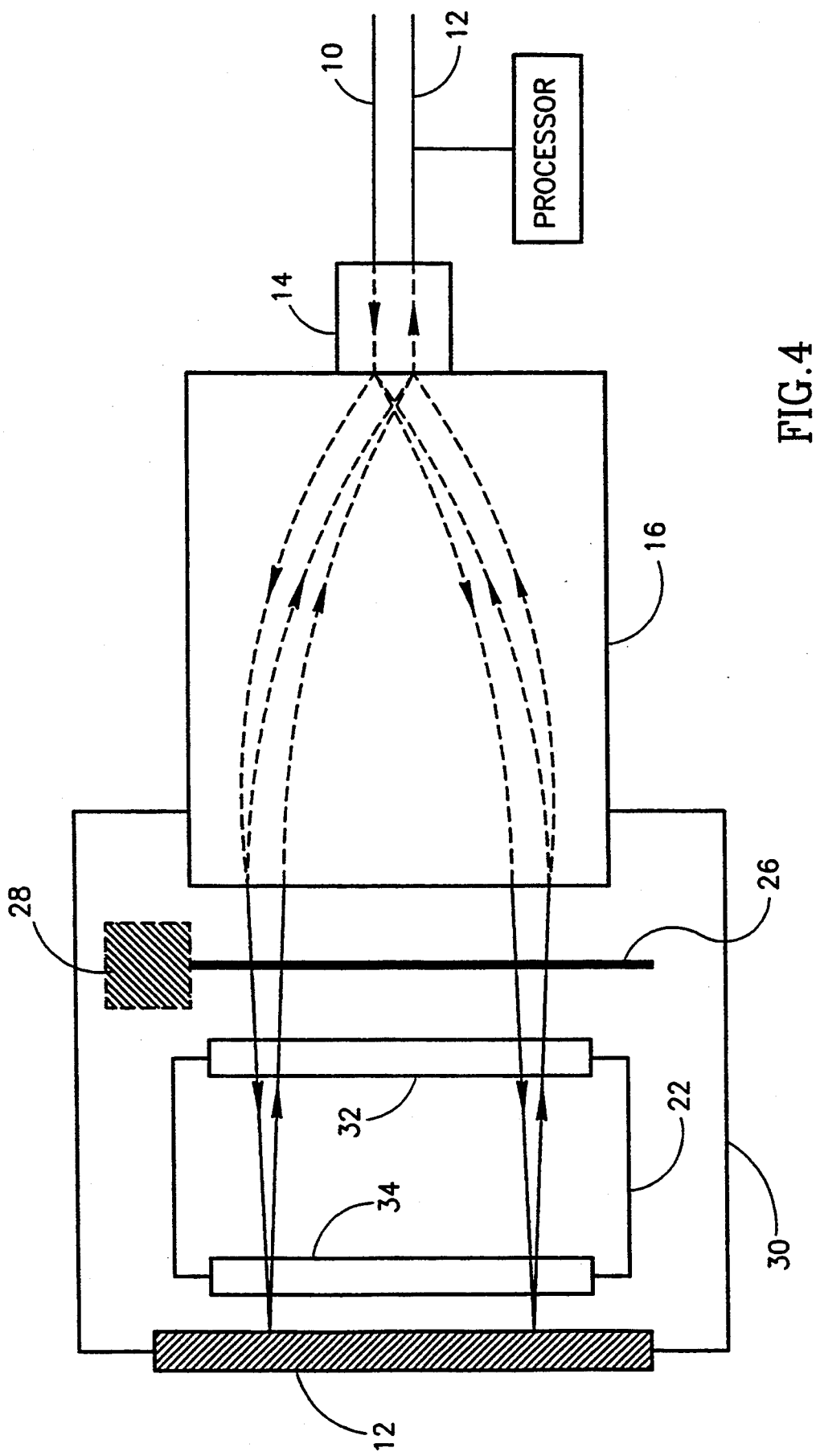
FIG. 4 is a schematic depiction of a device according to the present invention used as a dual beam transmission optical probe head.

Shown in FIG. 4 is a probe head according to the present invention for measuring transmission but which is self-referencing. The probe head is aligned so that the reflection from mirror 24 is focused into optical fiber 12. A suitable partition 26, preferably located in front of the sample compartment 22 within a housing 30, and operated by some suitable means such as a solenoid 28, is used to alternately block and unblock the optical axis or path of the light. Sample compartment 22 features optical windows 32 and 34 on its front and back surfaces. Approximately 5% of the signal is reflected back from the near surface of GRIN lens 16 into optical fiber 12. This portion of the signal is not transferred through the sample and is used for self-referencing the device. The absolute magnitude of the sample absorption can be deduced, for example, in the following way:

With partition 26 blocking the optical axis:

$$I_b = I_1 \times T_b \times R_b \times F_s$$

With partition 26 not blocking the optical axis:

$$I_t = I_1 \times (T_b \times R_b + T_t \times (R_b - 1)^2 \times T_{sample}) \times F_s$$

where, $I_b$ is the intensity of the signal reflected from the air/GRIN lens interface measured by the sensor;

$T_b$ is the optical transmission of the device for the $I_b$ beam;

$R_b$ is the reflection coefficient from the air/GRIN interface;

$I_1$ is the intensity of the signal reflected from the mirror and measured by the sensor; and $T_t$ is the optical transmission of the device for the $I_t$ beam $T_b$, $R_b$ and $T_t$ are constants. $I_1$ and $F_s$ are the functions which need to be eliminated from the equations, whereas $T_{sample}$ is the desired quantity.

$$(I_t \times I_b)/I_b = T_t/T_b \times (R_b - 1)^2/R_b \times T_{sample}$$

The constant $T_t/T_b \times (R_b - 1)^2/R_b$ can be deduced by performing the measurement once without sample ($T_{sample} = 1$), which yields the value of the constant.

$$T_{sample} = \{[I_b/(I_t - I_b](T_{sample} = 1)\} \times (I_t - I_b)/I_b$$

In this fashion it is possible to successfully eliminate the dependence of the fiber-analyzer optical response on the sample transmission.

A head probe according to the present invention can also be used in Raman spectroscopy. In certain applications it is desirable to carry out both Raman and transmission measurements on the same specimen. For example, transmission of visible light can give information regarding the electronic energy levels, while Raman spectroscopy gives information regarding the energy of vibrational levels.

The two measurements complement each other and can be used to deduce some important structural information of the molecules which would not be available if only one but not both of the measurements were performed. Usually, when both measurements are performed, the specimen is relocated from the Raman sample compartment to the transmission sample compartment in the Raman analyzer and transmission analyzer, respectively. In cases where in-line analysis is required, a unified probe capable of collecting Raman and transmission signals, or fluorescent and transmission signals, and guiding those signals to the appropriate systems is highly desired and is practicable with a head probe according to the present invention.

One example of an application where such a probe might be highly useful in the Raman and transmission spectroscopy in the analysis of octane number of motor gasoline.

It is well known that the quality factors of gasoline can be predicted by utilization of near infrared (NIR) transmission spectroscopy when coupled to a suitable calibration procedure.

The technique suffers from a basic limitation in that only overtones of a few C–H vibrations are observed in the NIR region, namely those of methyl, methylene, olefin, aromatics and naphthenes. Therefore, only predictions related to differences among hydrocarbon families such as paraffins isoparaffins, naphthenes, aromatics and olefins, can be ascertained. However, as is well known, the variation in the distribution of the different type molecules belonging to the same family can significantly alter the physical properties of the fuel.

For example, the two hydrocarbon solutions: (1) 50% n-pentane ($C_5H_{12}$) + 50% n-heptane ($C_7H_{16}$); and, (2)

100% n-hexane ($C_6H_{14}$) have very different vapor pressures and distillation points characteristics, and thus behave quite differently during processing and in engines. Nevertheless the NIR spectrum of the two solutions will be exactly the same because, on average, they have exactly the same type and number of C–H bonds, namely, four methyl bonds and two methylenes bonds. There is, therefor, no way to discriminate between the two solutions using NIR transmission spectroscopy.

Raman spectroscopy, on the other hand, is sensitive to C–R, C–C, C=C and vibrations associated with the entire molecule in addition to being sensitive to the C–H vibrations. Therefore, the Raman scattering spectrum exhibits the fingerprint of the different molecules making up the fuel, and is free from the limitation reported above. However, Raman scattering suffers from its own limitations. First, the signal to noise ratio of Raman scattering is poor in comparison to that of NIR absorption. Also, in some cases, the Raman spectrum suffers from excessive spectral information which might make negate the ability to use the measurement for quantitative analysis.

It is proposed to combine the two techniques for in-line analysis of the properties of gasoline derivatives. The fact that both techniques can be operated in the NIR spectral region, and can thus share the same type of fiber optics, as well as the same optical probe head, make it possible to combine the two into a single system having two complementary components. Since the NIR transmission technique demonstrates excellent quantitative analysis capabilities, while the Raman scattering technique demonstrates superb identification capabilities, the former can be used for the routine analysis while the latter can be used to conduct frequent validations of the former. The described combination technique gives a very powerful tool for reliable in-line process analysis.

Figure 5:
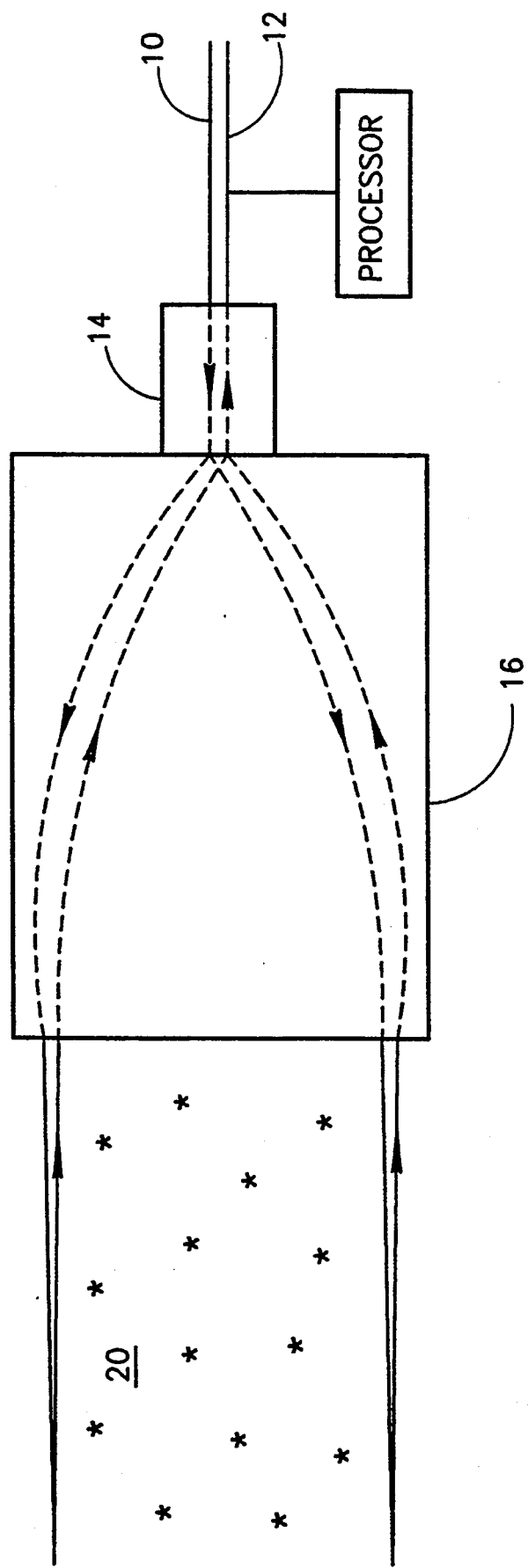
FIG. 5 is a schematic depiction of a device according to the present invention used as a single beam Raman or fluorescence optical probe head.

Shown in FIG. 5 is a device for measuring Raman or fluorescent signals from liquid specimens. A device such as that shown in FIG. 1 is used. The light emerging from optical fiber 10 is collimated by GRIN lens 16. The collimation is not strictly necessary for this application. However, with collimated light the collection efficiency of the scattered or emitted light is maximum since the overlap volume between the illuminated and collection volumes is the greatest.

The device is aligned in such a way that the reflection from the near surface of GRIN lens 16 will not focus back into optical fiber 12. This is done in order to reduce stray light. The scattered/emitted signal from the sample 20 is collected via GRIN lens 16 and is focused into optical fiber 12. In order to increase the collection efficiency, it is possible to add additional collection fibers parallel to the shown in FIG. 5.

One advantage of such Raman probe is that it examines a relatively large volume of the liquid and therefore it is not sensitive to the presence of small particulates and to inhomogeneities in the aqueous solution. Yet another advantage of the device is its long probing path length. This feature increases the intensity of the scattered signal simply because more molecules contribute to the signal by scattering light.

Figure 6:
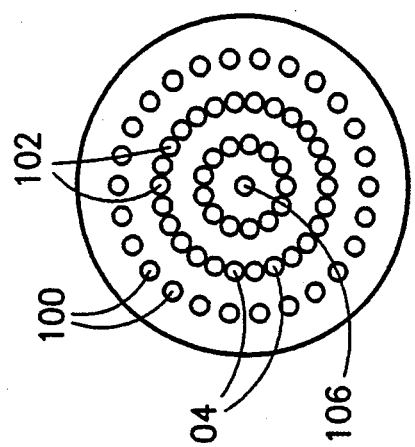
FIG. 6 is a plan view of a depth differential probe according to the present invention showing three concentric source fiber optic bundles.
Figure 7:
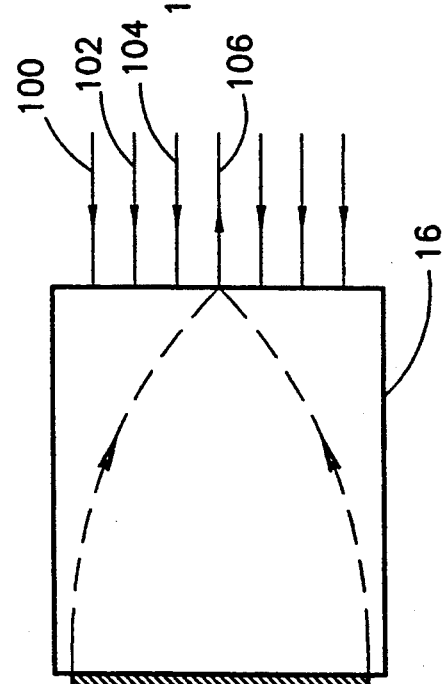
FIG. 7 is a side view of the probe of FIG. 6 also showing the regions of investigation of each of the three source fiber optic bundles.

Shown in FIGS. 6 and 7 are a plan view and a side view, respectively, of another embodiment of a probe according to the present invention which is similar to those described above but which may be used for the non-invasive scanning of a sample, which may, for example, be a living tissue. The Depth Differentiate Optical Probe (DDOP) may be based on various radiation types including, but not limited to, NIR diffuse reflection, Raman and fluorescence. Use of the device makes it possible to identify various organic and inorganic components at different depths of the sample without the need to physically penetrate the sample with the probe. Possible applications include the depth imaging of the interior of arteries and veins to measure the presence of drugs during transdermal drug delivery or measuring the glucose level in blood. Such a device can be installed on the edge of a coherent multi-strand fiber optics endoscope and can be used for in-vivo non-invasive monitoring of internal and external living portions of the human body.

As can be seen in the plan view of FIG. 6, a depth probe according to the present invention includes a number of optical fiber bundles. A plurality of optical fibers bring the radiation from the source to the sample. These are preferably arrayed in two or more concentric layers. In FIG. 6, three such concentric circles of optical fibers, an outer, an intermediate and an inner group, designated 100, 102 and 104, respectively, are shown. Centrally located is a single output optical fiber 106 which takes light reflected back from the sample to the detector (not shown).

The various optical bundles are glued, or otherwise connected to GRIN lens 16 in some suitable fashion. GRIN lens 16 is a collimated-type GRIN lens, preferably of about 0.25 pitch. Radiation leaving the far end of GRIN lens 16 is bent to an extent which depends on the radial distance of its entry point relative to the optical axis of GRIN lens 16. Thus, radiation coming in through any of outer optical fibers 100 will be bent to a much greater degree than radiation coming in through inner optical fibers 104. As a result, radiation input through outer optical fibers 100 will cover an area (designated '3' in FIG. 7) in the near vicinity of the far face of GRIN lens 16. Similarly, radiation coming in through intermediate optical fibers 102 will cover an area of greater depth into the sample (designated '3' and '2' in FIG. 7). Finally, radiation from inner optical fibers 104 will cover a region of even greater depth (designated '3', '2' and '1' in FIG. 7).

To compensate for the regions of overlap between the various regions, it is possible to quickly cycle the input radiation among the three (or more) concentric optical fiber sets. Thus, each of the outer optical fiber sets is sequentially activated in a rapid cycle. Radiation leaving the optical fibers leaves the far surface of GRIN lens 16 and enters the sample where it is partly reflected from particles in the sample. Some of the reflections enter the centrally located output optical fiber 106 and are lead to the detector (not shown). Since each of the sets of input fibers investigates a different portion, or depth, of the sample, it is possible to obtain information about the different regions of the sample, as explained next.

Figure 8:
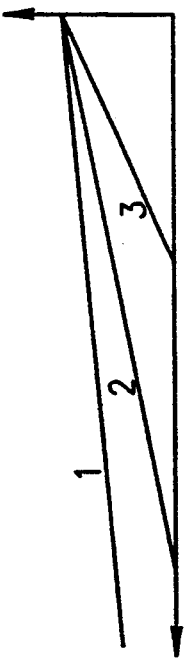
FIG. 8 is a schematic depiction of a possible output of the output central optical fiber.
Figure 9:
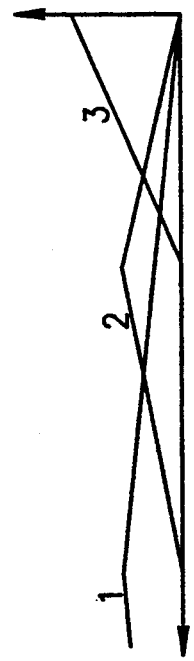
FIG. 9 is a schematic depiction of the possible result of the processing of the data of FIG. 8.

Shown schematically in FIG. 8 are the measured output signal as a function of depth for a given cycle of the input radiation. To obtain the true signal from region '3', which is investigated by each of the three sets of input optical fibers, it is necessary to subtract, for example, by using a suitable microprocessor, the reading of the intermediate and inner optical fibers from that of the outer optical fibers. Similarly, to obtain the true signal from region '2', which is investigated by both the intermediate and inner sets of input optical fibers, it is necessary to subtract the reading of the inner optical fibers from that of the intermediate optical fibers. The result is shown schematically in FIG. 9.

It will be readily appreciated that the optical fibers may be arranged on GRIN lens 16 in any of a number of suitable configurations, or contours. For example, the input fibers may be arranged in a line. Preferably, the input fibers are arranged in two or more concentric circles with the output fiber being centrally located. Clearly, the more concentric circles used, the better will be the depth resolution of the device.

While the invention has been described with respect to a limited number of embodiments, it will be appreciated that many variations, modifications and other applications of the invention may be made.

What is claimed is:

1. An optical probe head, comprising:
   (a) a gradient index lens, at least one face of which is in contact with the sample;
   (b) a plurality of transmitting optical fibers for inputting radiation into said gradient index lens in at least two optical locations of said gradient index lens;
   (c) at least one receiving optical fiber for receiving reflected radiation, said transmitting optical fibers and said at least one receiving optical fiber being fixedly held relative m said gradient index lens; and
   (d) means for processing said reflected radiation so as to obtain depth-related reflection information.

2. A probe head as in claim 1, wherein said transmitting optical fibers and said at least one receiving optical fiber are held in a ferule which is connected to said gradient index lens.

3. A probe head as in claim 1, wherein aligning of said optical fibers and said gradient index lens is effected by introducing radiation through one of said optical fibers, moving said optical fibers and said gradient index lens relative to each other until maximum radiation intensity is detected in the other of said optical fibers and fixing the position of said optical fibers and said gradient index.

4. A probe head as in claim 1, wherein said transmitting optical fibers are arranged in a plurality of sets, each of said sets being concentrically disposed about the optical axis of said gradient index lens.

5. A probe head as in claim 1, wherein said receiving optical fiber is a single fiber centrally located in said gradient index lens.

6. A probe head as in claim 4, wherein said receiving optical fiber is a single fiber centrally located in said gradient index lens.

7. A probe head as in claim 1, wherein the probe head forms a portion of an endoscope.

* * * * *